(12) United States Patent
Maeda (10) Patent No.: US 6,244,120 B1
(45) Date of Patent: Jun. 12, 2001

(54) APPARATUS AND METHOD FOR COUNTING NUMBER OF PARTICLES PRESENT IN COMPRESSED AIR, AND METHOD OF CONSTRUCTING COMPRESSED-AIR CLEANING SYSTEM

(75) Inventor: Sadao Maeda, Okazaki (JP)

(73) Assignees: Maeda Limited; Maeda Shell Service Co., Ltd., both of Okazaki (JP)

(*) Notice: Subject to any disclaimer, the term of this patent is extended or adjusted under 35 U.S.C. 154(b) by 0 days.

(21) Appl. No.: 09/482,377

(22) Filed: Jan. 13, 2000

(51) Int. Cl.$^7$ .................................................. G01N 1/00

(52) U.S. Cl. ........................................ 73/864.81; 73/865.5

(58) Field of Search .................... 73/28.01, 28.04–28.06, 73/865.5, 864.81, 863.83, 863.85; 356/440

(56) References Cited

U.S. PATENT DOCUMENTS

| | | |
|---|---|---|
| 4,487,618 | 12/1984 | Mann . |
| 4,897,094 | 1/1990 | Maeda . |
| 5,209,102 | * 5/1993 | Wang et al. ........................ 73/28.01 |
| 5,449,912 | * 9/1995 | Mayer . |

FOREIGN PATENT DOCUMENTS 2543671    4/1997  (JP) .

* cited by examiner

Primary Examiner—Robert Raevis
(74) Attorney, Agent, or Firm—Burr & Brown (57) ABSTRACT

An apparatus including a tube which is elastically deformable and which is connected to a compressed-air passage to introduce a compressed air therefrom, a pressure lowering device which is provided at a position corresponding to an intermediate portion of the tube, and which externally presses, and thereby elastically deforms, the intermediate portion of the tube to decrease a cross-sectional area of the intermediate portion, and thereby decrease an amount of the compressed air that flows through a downstream-side portion of the tube that is located on a downstream side of the intermediate portion in a flow direction in which the compressed air flows in the tube, so that a pressure of the compressed air in the downstream-side portion is lower than a pressure of the compressed air in an upstream-side portion of the tube, the tube having an air-leak opening which is provided in the downstream-side portion thereof and which allows a portion of the compressed air in the downstream-side portion to leak into the atmosphere, and a particle-number counter which sucks, in a state in which the portion of the compressed air in the downstream-side portion of the tube is allowed to leak into the atmosphere via the air-leak opening, the compressed air in the downstream-side portion and counts a number of particles present in the sucked compressed air.

5 Claims, 4 Drawing Sheets

APPARATUS AND METHOD FOR COUNTING NUMBER OF PARTICLES PRESENT IN COMPRESSED AIR, AND METHOD OF CONSTRUCTING COMPRESSED-AIR CLEANING SYSTEM

BACKGROUND OF THE INVENTION

Field of the Invention

The present invention relates to an apparatus and a method for counting a number of particles present in a compressed air, and a method of constructing a compressed-air cleaning system, and particularly to an apparatus and a method for sucking a compressed air introduced from a compressed-air passage and counting a number of particles present in the sucked compressed air, and a method of constructing a compressed-air cleaning system by using at least one removing device which removes particles from a compressed air.

Related Art Statement

Conventionally, many factories have been equipped with compressed-air operated devices and/or compressed-air jetting devices in which compressed air is used as a working medium or fluid. The compressed-air operated devices, the compressed-air jetting devices, or other compressed-air using devices are operated or driven, as being well known in the art, by the pressure energy of compressed air that is supplied thereto from a compressed-air source (e.g., air compressor) via a compressed-air supply pipeline (i.e., a compressed-air passage). However, when the compressed-air using devices are operated, the compressed air cannot be prevented from being contaminated with contaminating matter, such as lubricant used, or rust produced, in the compressed-air source and/or the compressed-air supply pipeline. If the compressed air is mixed with much of the contaminating matter, then the compressed-air using devices may malfunction or fall in disorder. In the case where the compressed-air using devices are used in a food production line, the safety of the food products may be adversely influenced.

Hence, generally, in factories equipped with compressed-air operated devices and/or compressed-air jetting devices, one or more removing devices which remove contaminating matter are provided at one or more locations on a compressed-air supply pipeline to prevent the contamination of compressed air.

However, almost all of those removing devices are ones each of which employs a filter for filtering compressed air to catch particles of contaminating matter present in the compressed air and thereby clean the compressed air, and the cleaning capability of the filter inevitably decreases as the time of use of the filter increases.

Hence, in some factories, it has been practiced that the cleanliness of compressed air is measured periodically or non-periodically, by counting a number of particles present in a compressed air flowing in a compressed-air supply pipeline, using a particle-number counting device such as a so-called particle counter which is mainly used to count a number of particles present in a clean room of each factory. Based on the measured cleanliness, the respective filters of the removing devices may be replaced with new ones, to maintain or control a high cleanliness of the compressed air.

However, a conventional particle-number counting device, such as a conventional particle counter, is designed to suck, through its suction inlet, a normal-pressure air in a clean room and count a number of particles present in the sucked air. Accordingly, if the counting device sucks a compressed air having a high pressure, it may be damaged or disordered. Even if the counting device may not be damaged or disordered, it may not count an accurate particle number, because it may suck an excessive amount of air.

In order to avoid the above-indicated problem, a pressure-resistant hollow case is employed which has a prescribed capacity and has an introduction inlet for introducing a compressed air. More specifically described, a compressed air is introduced from a compressed-air passage into the pressure-resistant case through the introduction inlet, and the pressure of the compressed air is lowered in the case. After the pressure-resistant case is filled with the compressed air whose pressure has been lowered, the compressed air in the case is sucked by the particle-number counting device, and a number of particles present in the sucked air is counted by the counting device. However, the conventional particle-number counting device employing the pressure-resistant case has some problems.

First, the pressure-resistant case employed in the conventional particle-number counting device needs a considerably large capacity for the purpose of sufficiently lowering the pressure of the compressed air introduced. Accordingly, the particle-number counting device including the pressure-resistant case is inevitably large-sized, which reduces the ease of use. Second, since the counting device can count a number of particles present in a compressed air after the air remaining in the large-sized pressure-resistant case is exchanged with the compressed air and the case is filled with the compressed air, it needs a long time before the counting device is prepared to start counting a particle number, which reduces the efficiency of operation.

Moreover, in many cases, a random number of above-indicated removing device or devices is or are provided at a random position or positions on the compressed-air supply pipeline of each factory, irrespective of how the compressed air flowing in the supply pipeline is actually contaminated. Thus, the total number of the removing devices and/or the positions where the removing devices are provided may not appropriately correspond to the actual condition of contamination of the compressed air, and accordingly the compressed air may not be effectively cleaned by the removing devices.

SUMMARY OF THE INVENTION

It is therefore a first object of the present invention to provide an apparatus for quickly and accurately counting a number of particles present in a compressed air and which enjoys a high degree of compactness and a high ease of use.

It is a second object of the present invention to provide a method of quickly and accurately counting a number of particles present in a compressed air.

It is a third object of the present invention to provide a method of constructing a cleaning system which effectively cleans a compressed air flowing in a compressed-air supply pipeline, based on how the compressed air in the supply pipeline is actually contaminated.

According to a first aspect of the present invention, there is provided an apparatus for counting a number of particles present in a compressed air introduced from a compressed-air passage, the apparatus comprising an introduction tube which is elastically deformable and which is connected to the compressed-air passage to introduce the compressed air therefrom; a pressure lowering device which is provided at a position corresponding to an intermediate portion of the introduction tube, and which externally presses, and thereby elastically deforms, the intermediate portion of the tube to decrease a cross-sectional area of the intermediate portion, and thereby decrease an amount of the compressed air that flows through a downstream-side portion of the tube that is located on a downstream side of the intermediate portion in a flow direction in which the compressed air flows in the tube, so that a pressure of the compressed air in the downstream-side portion of the tube is lower than a pressure of the compressed air in an upstream-side portion of the tube that is located on an upstream side of the intermediate portion in the flow direction; the introduction tube having an air-leak opening which is provided in the downstream-side portion thereof and which allows a portion of the compressed air in the downstream-side portion to leak into an atmosphere; and a particle-number counter which sucks, in a state in which the portion of the compressed air in the downstream-side portion of the introduction tube is allowed to leak into the atmosphere via the air-leak opening, the compressed air in the downstream-side portion and counts a number of particles present in the sucked compressed air.

In short, the particle-number counting apparatus according to the present invention, is operated such that in the state in which the compressed air is introduced from the compressed-air passage into the introduction tube, the intermediate portion of the elastically deformable introduction tube is externally pressed by the pressure lowering device, and thereby elastically deformed, so that the cross-sectional area of the tube is decreased, accordingly the amount of the compressed air that flows in the downstream-side portion of the introduction tube, located on the downstream side of the above intermediate portion thereof, is decreased, and accordingly the pressure of the compressed air in the downstream-side portion of the tube is lowered, and such that in the state in which a portion of the compressed air whose pressure has been lowered is allowed to leak into the atmosphere through the air-leak opening provided in the downstream-side portion of the tube, the compressed air is sucked by the particle-number counter and a number of particles present in the sucked air is counted by the same.

Thus, the present particle-number counting apparatus includes the pressure lowering device which lowers the pressure of the compressed air introduced from the compressed-air passage into the introduction tube, and the particle-number counter sucks the compressed air whose pressure has been lowered by the pressure lowering device. Therefore, even in the case where the particle-number counter is provided by a common counting device, such as a so-called particle counter, which has no special pressure-resistant structure, the common counting device is very effectively prevented from being damaged or disordered by the pressure of the compressed air sucked. In addition, the particle-number counter is effectively prevented from sucking an excessive amount of air that is much more than an amount of air prescribed to be suitable for the counter to count an accurate particle number. Therefore, the particle-number counter is prevented from counting an inaccurate particle number resulting from the suction of excessive amount of air. That is, the present apparatus can surely provide respective accurate particle numbers.

In the present apparatus, the particle-number counter sucks the compressed air in the state in which a portion of the compressed air whose pressure has been lowered is allowed to leak into the atmosphere through the air-leak opening of the introduction tube. Accordingly, a user or an operator can easily and surely lower the pressure of the compressed air, down to a value appropriately corresponding to the air-sucking capability of the particle-number counter, while he or she estimates which value the pressure of the compressed air is now taking, by just observing the amount of air leaking from the air-leak opening. To this end, the operator has only to adjust the amount of elastic deformation of the intermediate portion of the introduction tube caused by the pressure lowering device, that is, the cross-sectional area of the intermediate portion, and thereby adjust the amount of the compressed air that flows in the downstream-side portion of the tube located on the downstream side of the intermediate portion thereof. Thus, the present apparatus can be easily operated to count respective highly reliable particle numbers in a stable manner.

Since the present particle-number counting apparatus includes, as described above, the pressure lowering device for lowering the pressure of the compressed air, it need not employ a large-capacity pressure-resistant case for lowering the pressure of the compressed air, in contrast to the conventional particle-number counting device. In addition, since the introduction tube is elastically deformable as described above, and the pressure lowering device has a simple structure for just externally pressing the tube, both the tube and the pressure lowering device, and the invention apparatus as a whole including those elements, enjoy a high degree of compactness, which contributes to improving the ease of use.

Moreover, in the present apparatus, the pressure of the compressed air flowing in the downstream-side portion of the introduction tube, located on the downstream side of the intermediate portion of the tube, can be instantly lowered by just operating the pressure lowering device to press, and elastically deform, the intermediate portion of the tube and thereby decrease the cross-sectional area of the tube. Thus, the present apparatus can instantly start counting a number of particles present in the compressed air. This is contrast to the conventional device which, before starting counting a particle number, must carry out a time-consuming and cumbersome preparation operation in which the air remaining in the large-capacity pressure-resistant case must be exchanged with the compressed air. Thus, in the present apparatus, the time needed to carry out the preparation operation before the particle-number counting can be significantly decreased, and the work needed to carry out the same is also decreased. Thus, the present apparatus can much more quickly and easily carry out the particle-number counting operation than the conventional device.

Furthermore, in the invention apparatus, the pressure of the compressed air is lowered by operating the pressure lowering device to press externally the intermediate portion of the introduction tube. Accordingly, the compressed air flowing in the tube is prevented from being contaminated with particles of sticking matter, such as lubricant or dust, sticking to the pressure lowering device, in stark contrast to a particular case where a pressure lowering device, such as a flow-amount control valve (e.g., a ball valve), is provided inside the intermediate portion of the tube and is externally controlled to change the cross-sectional area of the intermediate portion. That is, the present apparatus can count an accurate particle number which is not adversely influenced by the particles of the sticking matter sticking to the pressure lowering device.

Thus, the particle-number counting apparatus in accordance with the present invention can quickly and easily count an accurate and reliable number of particles present in the compressed air introduced from the compressed-air passage, and can enjoy, as a whole, a high degree of compactness and accordingly enjoy a high ease of use or handling.

According to a preferred feature of the first aspect of the present invention, the pressure lowering device comprises two members which are provided on both sides of the intermediate portion of the introduction tube such that the two members are opposed to each other via the intermediate portion and are movable toward, and away from, each other; and an operable member which is operable to move the two members toward, and away from, each other, when the operable member is operated to move the two members toward each other, the two members sandwich, and thereby elastically deform, the intermediate portion of the introduction tube to decrease the cross-sectional area of the intermediate portion. With this arrangement, the operability of the pressure lowering device and accordingly the operability of the present apparatus as a whole are much improved.

According to a second aspect of the present invention, there is provided a method of counting a number of particles present in a compressed air, by using a particle- number counter which sucks the compressed air introduced from a compressed-air passage and counts the number of particles present in the sucked compressed air, the method comprising the steps of connecting an elastically deformable, introduction tube to the compressed-air passage, to introduce the compressed air from the passage into the tube, externally pressing, and thereby elastically deforming, an intermediate portion of the introduction tube to decrease a cross-sectional area of the intermediate portion, and thereby decrease an amount of the compressed air that flows through a downstream-side portion of the tube that is located on a downstream side of the intermediate portion in a flow direction in which the compressed air flows in the tube, so that a pressure of the compressed air in the downstream-side portion of the tube is lower than a pressure of the compressed air in an upstream-side portion of the tube that is located on an upstream side of the intermediate portion in the flow direction, and operating, in a state in which a portion of the compressed air in the downstream-side portion of the introduction tube is allowed to leak into an atmosphere via an air-leak opening provided in the downstream-side portion, the particle-number counter to suck the compressed air in the downstream-side portion and count a number of particles present in the sucked compressed air.

Since the particle-number counting method in accordance with the present invention does not need the above-described cumbersome and time-consuming preparation operation in which the large-capacity and pressure-resistant case is used, it assures that a number of particles present in the compressed air is counted with ease and in a short time. In addition, since no excessive amount of the compressed air is sucked, a number of particles present in an appropriate amount of the compressed air is counted.

Thus, the present particle-number counting method assures that a number of particles present in the compressed air is counted quickly and easily, and that the reliability of the counted particle number is significantly improved.

According to a third aspect of the present invention, there is provided a method of constructing a compressed-air cleaning system, by providing at least one removing device at least one position on a compressed-air supply pipeline which connects between a compressed-air source and at least one compressed-air using device, so that the removing device removes particles present in a compressed air supplied from the compressed-air source to the compressed-air using device via the compressed-air supply pipeline, and thereby cleans the compressed air, connecting an elastically deformable, introduction tube to each of a plurality of arbitrarily selected portions of the compressed-air supply pipeline, to introduce the compressed air from the pipeline into the tube, externally pressing, and thereby elastically deforming, an intermediate portion of the introduction tube to decrease a cross-sectional area of the intermediate portion, and thereby decrease an amount of the compressed air that flows through a downstream-side portion of the tube that is located on a downstream side of the intermediate portion in a flow direction in which the compressed air flows in the tube, so that a pressure of the compressed air in the downstream-side portion of the tube is lower than a pressure of the compressed air in an upstream-side portion of the tube that is located on an upstream side of the intermediate portion in the flow direction, operating, in a state in which a portion of the compressed air in the downstream-side portion of the introduction tube is allowed to leak into an atmosphere via an air-leak opening provided in the downstream-side portion, a particle-number counter to suck the compressed air in the downstream-side portion and count a number of particles present in the sucked compressed air, so as to obtain a plurality of sets of particle-number data each of which is indicative of the counted number of particles present in the compressed air introduced from a corresponding one of the plurality of portions of the compressed-air supply pipeline, determining, based on the obtained sets of particle-number data, the at least one position on the compressed-air supply pipeline where the at least one removing device is to be provided to effectively clean the compressed air to be supplied to the compressed-air using device, and providing the at least one removing device at the at least one determined position on the compressed-air supply pipeline.

In short, in the compressed-air-cleaning-system constructing method in accordance with the present invention, the method capable of quickly and accurately measuring the number of particles present in the compressed air is employed to obtain the plurality of sets of particle-number data indicative of the respective particles numbers measured at the plurality of positions on the compressed-air supply pipeline, the thus obtained sets of particle-number data are used to determine, on the supply pipeline, one or more particular positions where one or more particle removing devices are to be provided, and the particle removing device or devices is or are provided at the thus determined particular position or positions, respectively. Thus, the present method assures that the actual condition of contamination of the compressed air at an arbitrary position on the supply pipeline is accurately diagnosed and an appropriate number of particle removing device or devices is or are provided at an appropriate position or positions on the supply pipeline.

Therefore, in a compressed-air cleaning system constructed by the present constructing method, the compressed air can be effectively and reliably cleaned according to the accurate condition of contamination of the compressed air that is diagnosed based on the accurate counted number of particles present in the compressed air introduced from each of respective portions of the supply pipeline.

According to a preferred feature of the third aspect of the present invention, the compressed-air supply pipeline comprises a main pipe which is connected to the compressed-air source, and a plurality of branch pipes each of which is connected to the main pipe and which are connected to a plurality of compressed-air using devices, respectively.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Hereinafter, there will be described in detail an apparatus and a method for counting a number of particles present in a compressed air, and a method of constructing a compressed-air cleaning system, each embodying the present invention, by reference to the drawings.

Figure 1:
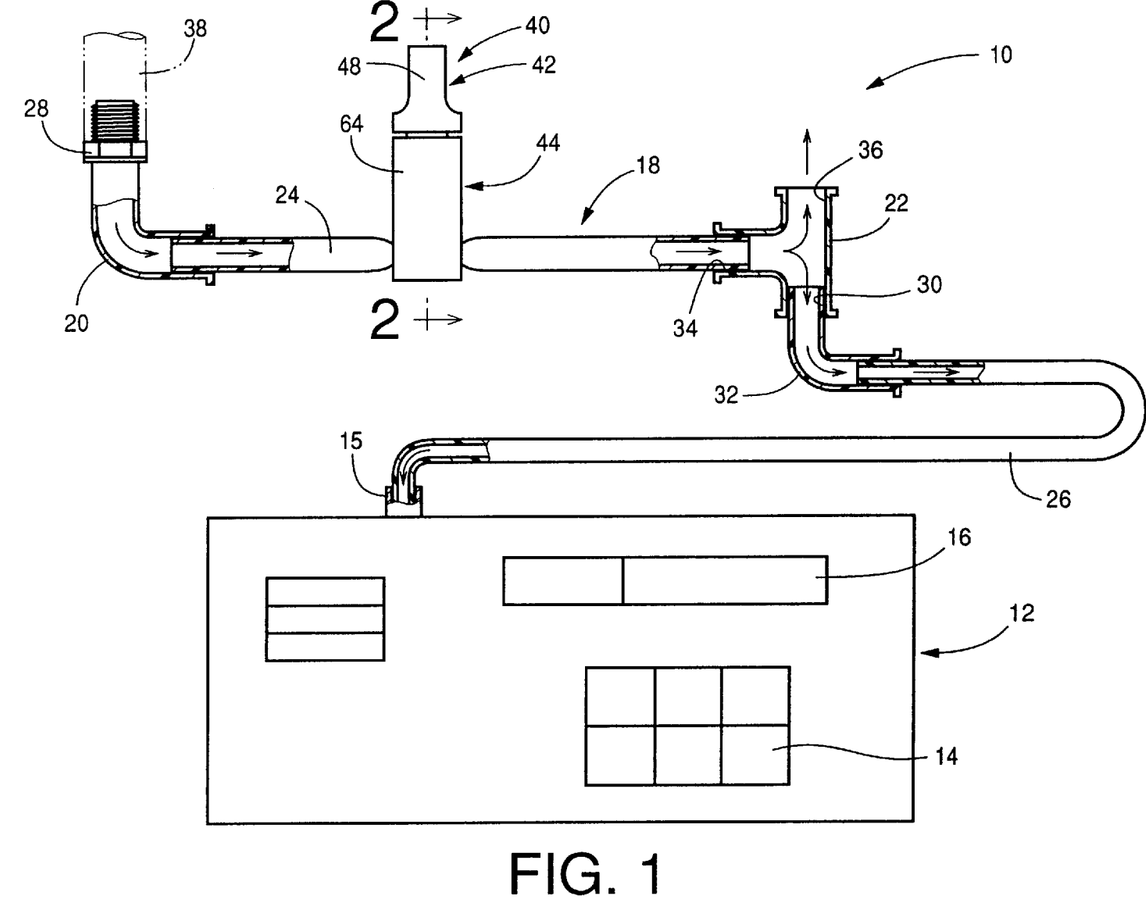
FIG. 1 is a partly cross-sectioned, schematic front elevation view of a particle-number counting apparatus which embodies the present invention and which carries out a particle-number, counting method embodying the present invention.

First, FIG. 1 schematically shows an example of an apparatus which counts a number of particles present in a compressed air and which has a construction according to the present invention, that is, a particle-number counting apparatus 10 including a particle counter 12.

More specifically described, the particle counter 12 is provided by a laser particle counter which counts a number of particles present in an air under an atmospheric pressure and which has a construction known in the art. Though not shown in the drawings, the particle counter 12 includes an air sucker which sucks an ambient air, and a number counter which counts a number of particles present in the sucked air, based on a laser light which is emitted toward the particles and then diffused by the same. When a manually operable panel 14 of the particle counter 12, provided in a front surface thereof, is operated by a user in a prescribed manner, the air sucker sucks an air from outside through a suction inlet 15, and the number counter counts a number of particles present in the sucked air. A display 16, provided above the operation panel 14, displays or indicates the thus counted particle number.

In the present embodiment, an introduction tube 18 is connected to the suction inlet 15 of the particle counter 12 constructed as described above.

The introduction tube 18 includes an upstream-side joint 20, a downstream-side joint 22, an upstream-side pipe 24, and a downstream-side pipe 26. The upstream-side joint 20 is provided by an elbow formed of a resin, and a nipple 28 formed of a metal is permanently fixed to one end opening of the elbow, i.e., the joint 20, such that one end portion of the nipple 28 is exposed outside. The downstream-side joint 22 is provided by a T-shaped joint which is formed of a resin and which includes three openings. One of the three openings of the downstream-side joint 22 provides a downstream-side pipe connection 30 in which one end portion of an elbow 32 formed of a resin is inserted such that the elbow 32 is rotatable relative to the pipe connection 30 about an axis line of the same 30 but cannot easily come off the same 30. One of the other two openings of the downstream-side joint 22 provides an upstream-side pipe connection 34 which has the same inner diameter as that of the other end opening of the upstream-side joint 20 that is opposite to the above-indicated one end opening of the same 20 to which the nipple 28 is attached. The third opening of the downstream-side joint 22 provides an air-leak opening 36 which will be described later.

Each of the upstream-side and downstream-side pipes 24, 26 is formed of a urethane resin to have a thick wall, and accordingly has both elasticity and pressure resistance. Thus, each pipe 24, 26 allows a compressed air to flow therethrough, and is elastically deformable. The upstream-side pipe 24 has a prescribed length, and an outer diameter which allows the pipe 24 to be press-fitted in each of the above-indicated other end opening of the upstream-side joint 20 and the upstream-side pipe connection 34 of the downstream-side joint 22. The downstream-side pipe 26 has a length greater than that of the upstream-side pipe 24, and has an outer diameter which allows the pipe 26 to be press-fitted in each of the other end opening of the elbow 32 attached to the downstream-side pipe connection 30 of the downstream-side joint 22 and the suction inlet 15 of the particle counter 12.

The upstream-side pipe 24 constructed as described above is press-fitted and fixed, at one end portion thereof, in and to the other end opening of the upstream-side joint 20 to which the nipple 28 is not attached, and is press-fitted and fixed, at the other end portion thereof, in and to the upstream-side pipe connection 34 of the downstream-side joint 22, in a state in which the upstream-side joint 20, the upstream-side pipe 24, and the downstream-side joint 22 are communicated with one another. The downstream-side pipe 26 is press-fitted and fixed, at one end portion thereof, in and to the other end opening of the elbow 32 which is connected, at the one end opening thereof, to the downstream-side joint 22, in a state in which the downstream-side joint 22 and the downstream-side pipe 26 are communicated with each other.

Thus, the introduction tube 18 is provided by assembling the upstream-side joint 20, the upstream-side pipe 24, the downstream-side joint 22, and the downstream-side pipe 26, in a state in which the joints and pipes 20, 24, 22, 26 are communicated with one another, the one end opening of the upstream-side joint 20 to which the nipple 28 is attached opens outside, the air-leak opening 36 opens outside, and the other end opening of the downstream-side pipe 26 that is opposite to the one end opening thereof fixed to the downstream-side joint 22 opens outside. This introduction tube 18 is connected, at the other end opening of the downstream-side pipe 26 that opens outside, to the suction inlet 15 of the air sucker of the particle counter 12, in a state in which the tube 18 is communicated with the counter 12.

In the present embodiment, the introduction tube 18 is connected, at the nipple 28 attached to the one end opening of the upstream-side joint 20, a compressed-air passage 38, indicated at phantom line in FIG. 1, in which a compressed air flows, in a state in which the tube 18 is communicated with the atmosphere via the air-leak opening 36. Thus, the compressed air flowing in the compressed-air passage 38 is introduced into the upstream-side joint 20 of the introduction tube 18, and further guided to the particle counter 12 via the upstream-side pipe 24 and the downstream-side joint and pipe 22, 26, as indicated at arrows in FIG. 1. While the compressed air flows through the downstream-side joint 22, a portion of the compressed air leaks into the atmosphere via the air-leak opening 36 of the joint 22.

Figure 2:
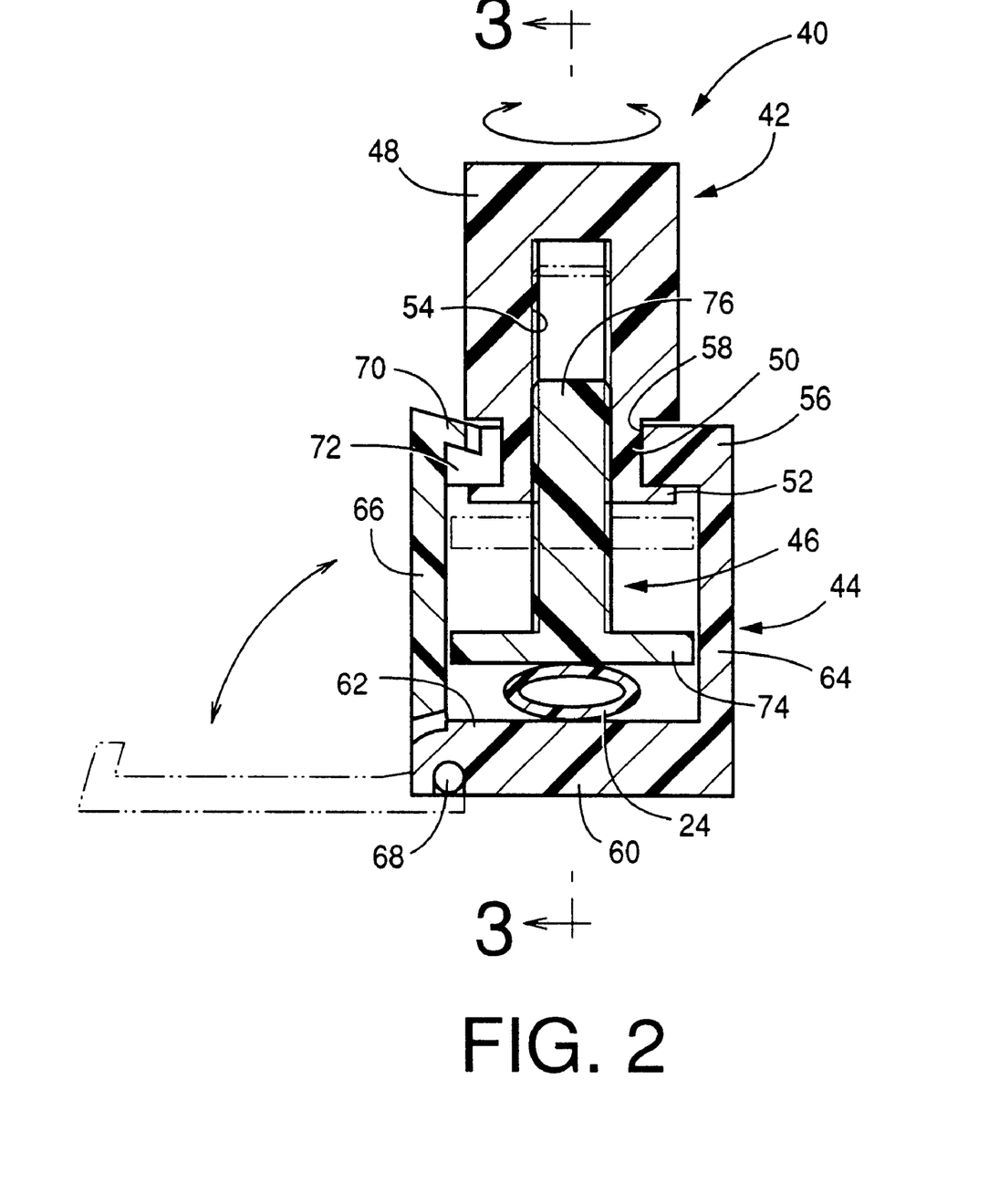
FIG. 2 is a cross-sectioned side elevation view of a pinch-valve device of the particle-number counting apparatus of FIG. 1, taken along 2—2 in FIG. 1.
Figure 3:
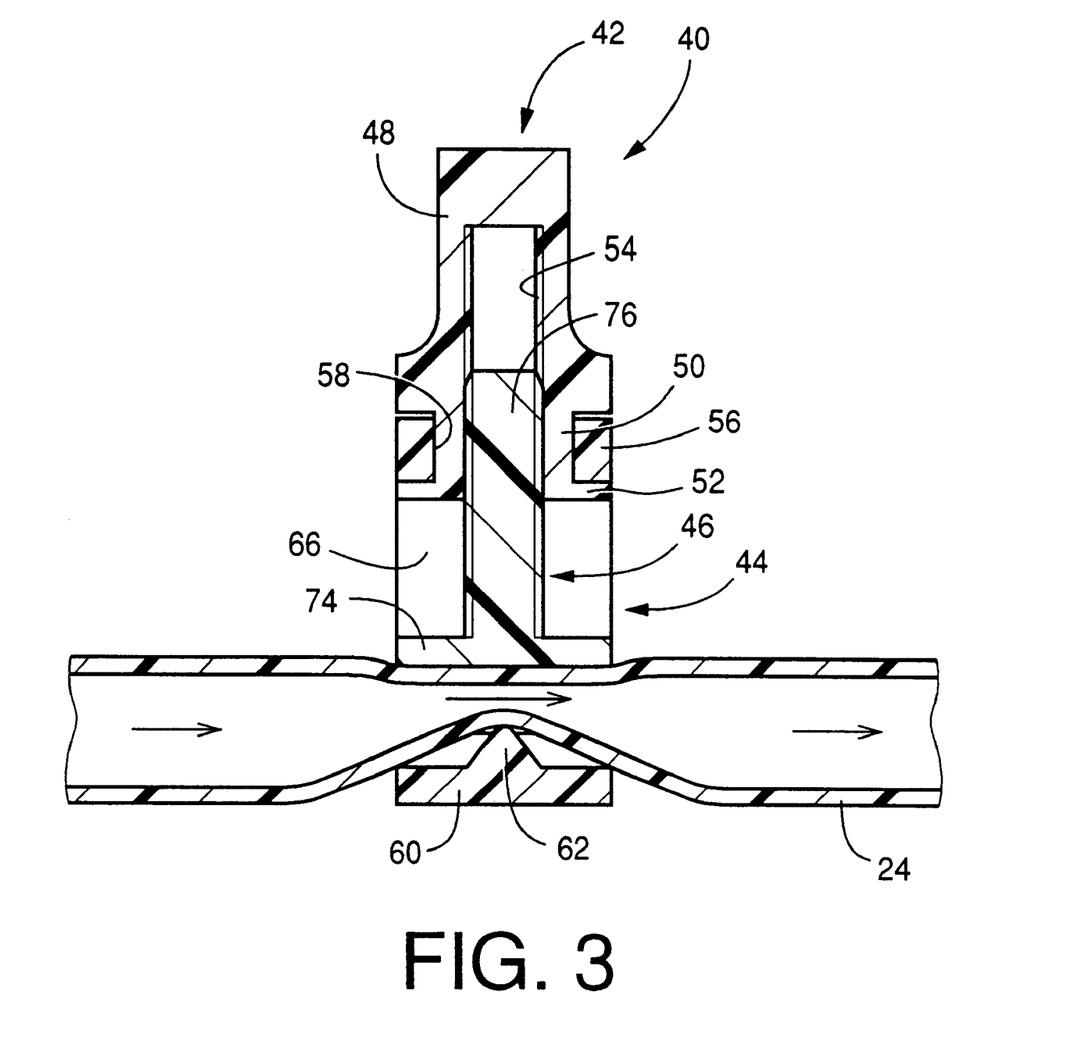
FIG. 3 is a cross-sectioned side elevation view of the pinch-valve device of FIG. 2, taken along 3—3 in FIG. 2.

A pinch-valve device 40 as a pressure lowering device is provided at a position corresponding to a substantially middle portion of the upstream-side pipe 24 as an intermediate portion of the introduction tube 18 constructed as described above. As shown in FIGS. 2 and 3, the pinch-valve device 40 includes a rotatable member 42 as a manually operable member, and a support member 44 and a valve member 46 as two members which are opposed to each other. The rotatable member 42 has a generally cylindrical shape, and includes a knob 48 showing a shape which may be obtained by cutting off a pair of diametrically opposite, upper, peripheral portions of the cylindrical shape. The rotatable member 42 additionally includes a cylindrical axis portion 50 which extends from a lower surface of the knob 48 and which has a diameter smaller than that of the same 48; and an outer flange 52 which is formed integrally with the axis portion 50 so as to project radially outward from an outer circumferential surface of a lower end portion of the axis portion 50 and continuously extend in a circumferential direction of the same 50. The rotatable member 42 has an internally threaded hole 54 formed in a central portion of a lower surface of the member 42. The hole 54 is so deep as to reach an upper portion of the knob 48.

The support member 44 has a rectangular frame-like shape having four walls. An upper wall 56 as one of the four walls of the support member 44 has a recess 58 having a width which is somewhat greater than the outer diameter of the axis portion 50 of the rotatable member 42 and is smaller by a prescribed dimension than the outer diameter of each of a lower portion of the knob 48 and the outer flange 52. A lower wall 60 as another of the four walls of the support member 44 has, on a middle portion of an upper surface thereof, a straight ridge 62 which is formed integrally with a remaining portion of the wall 60 so as to extend continuously in a lengthwise direction of the wall 60, and which has a triangular transverse cross sections as shown in FIG. 3. One side wall 64 is formed integrally with the upper wall 56 and the lower wall 60, so as to connect between the two walls 56, 60. The other side wall 66 is attached to the lower wall 60, such that the other side wall 66 is pivotable about an axis member 68 provided in a lower portion thereof. Thus, the framework of the support member 44 is opened and closed when the other side wall 66 is pivoted downward and upward, respectively. When the other side wall 66 is pivoted upward to close the framework of the support member 44, a side-wall-side engaging projection 70 provided in an upper end portion of the other side wall 60 engages an upper-wall-side engaging recess 72 provided in the upper wall 56.

The valve member 46 includes a thick rectangular press plate 74 which horizontally extends to part clearly an inner space of the framework of the support member 44 into an upper room and a lower room; and a screw 76 which integrally projects over a prescribed length from a central portion of an upper surface of the press plate 74 and which is externally threaded in an outer circumferential surface thereof over an entire length thereof.

The rotatable member 42 is supported by the support member 44, such that the axis portion 50 of the rotatable member 42 is inserted in the recess 58 of the upper wall 56 of the support member 44 and such that the rotatable member 42 is rotatable relative to the upper wall 56 and is vertically immovable relative to the same 56. In addition, the press plate 74 of the valve member 46 is provided in the inner space of the support member 44, and the valve member 46 is attached to the rotatable member 42 such that the externally threaded screw 76 of the valve member 46 is screwed in the internally threaded hole 54 of the rotatable member 42.

When a user turns or rotates, with his or her fingers, the knob 48 of the rotatable member 42, clockwise or counterclockwise, the screw 76 of the valve member 46 is fed out of, or screwed into, the hole 54 of the rotatable member 42, respectively, by an amount corresponding to the amount of rotation of the knob 48, so that the valve member 46 as a whole is moved downward or upward, respectively, and accordingly the press plate 74 is moved toward, or away from, the lower wall 60 of the support member 44, respectively.

In the present embodiment, the pinch-valve device 40 is provided in the vicinity of the intermediate portion of the introduction tube 18, such that the middle portion of the upstream-side pipe 24 of the tube 18 is positioned between the press plate 74 of the valve member 46 and the lower wall 60 of the support member 44. When the rotatable member 42 is full-rotated clockwise by a prescribed number of times by the user, the lower surface of the press plate 74 and the top portion of the ridge 62 of the lower wall 60 cooperate with each other to press externally and vertically the middle portion of the upstream-side pipe 24 and thereby flatten or narrow the pipe 24 by a prescribed amount, i.e., elastically deform the pipe 24 and thereby decrease a cross-sectional area of the pipe 24 through which the compressed air can flow.

Thus, in the present particle-number counting apparatus 10, an amount of the compressed air that is introduced into the upstream-side joint 20 of the introduction tube 18 and then flows in a downstream-side portion of the upstream-side pipe 24 that is located on a downstream side of the middle portion of the pipe 24 elastically deformed by the pinch-valve device 40 to decrease the cross-sectional area thereof, is smaller than an amount of the compressed air that flows in an upstream-side portion of the pipe 24 that is located on an upstream side of the middle portion of the pipe 24 in a flow direction in which the compressed air flows. Accordingly, a pressure of the compressed air in the downstream-side portion of the pipe 24 is lower than a pressure of the compressed air in the upstream-side portion of the pipe 24, by an amount corresponding to an amount of elastic deformation of the middle portion of the pipe 24. A portion of the compressed air whose pressure has thus been lowered is sucked from the introduction tube 18 by the air sucker of the particle counter 12, in a state in which the excessive or remaining portion of the compressed air is allowed to leak into the atmosphere via the air-leak opening 36 of the downstream-side joint 22, so that a number of particles present in a prescribed unit volume of the sucked compressed air is counted by the number counter of the particle counter 12.

When the user rotates the rotatable member 42 of the pinch-valve device 40 counterclockwise, the rectangular press plate 74 of the valve member 46 is moved away from the lower wall 60 of the support member 44, so that the middle portion of the elastically deformable upstream-side pipe 24 returns, owing to its elastic restoring force, to its original shape. Accordingly, the cross-sectional area of the middle portion of the pipe 24 can be easily adjusted by changing the direction (i.e., clockwise or counterclockwise) of rotation of the rotatable member 42 of the pinch-valve device 40 and/or changing (i.e., increasing or decreasing) the amount of rotation (or the number of full rotation) of the rotatable member 42. When the user rotates the rotatable member 42 counterclockwise by a certain amount to move the valve member 46 upward over a certain distance, as indicated at phantom line in FIG. 2, and pivots the other side wall 66 of the support member 44 downward to its horizontal posture, the middle portion of the pipe 24 is released from the pressing force applied thereto from the press plate 74 of the valve member 46 and the lower wall 60 of the support member 44. In this state, the user can remove the thus opened framework of the support member 44 from the middle portion of the pipe 24, that is, removes the middle portion of the pipe 24 from the space between the press plate 74 of the valve member 46, and the lower wall 60 of the support member 44, of the pinch valve device 40.

Hereinafter, there will be described the operation of the particle-number counting apparatus 10, constructed as described above, for carrying out a method of counting a number of particles present in the compressed air flowing in the compressed-air passage 38.

First, the user closes the framework of the pinch-valve device 40 provided at a position corresponding to the middle portion of the upstream-side pipe 24 of the introduction tube 18. That is, the user rotates the rotatable member 42 clockwise to elastically deform the middle portion of the pipe 24 and thereby decrease the cross-sectional area of the pipe 24 to a very small value or zero. Subsequently, the user starts the operation of the air sucker of the particle counter 12.

Next, the user attaches the upstream-side joint 20 of the introduction tube 18 to the compressed-air passage 38 via the nipple 28, so that the compressed air in the passage 38 is introduced into the tube 18. In this state, an amount or a pressure of the compressed air that flows in the downstream-side portion of the upstream-side pipe 24 of the tube 18 that is located on the downstream side of the middle portion of the pipe 24 elastically deformed by the pinch-valve device 40 is much lower than those of the compressed air that flows in the upstream-side portion of the pipe 24 that is located on the downstream side of the middle portion of the pipe 24, by respective amounts corresponding to the amount of elastic deformation of the middle portion, or the compressed air is completely inhibited from flowing from the upstream-side portion of the pipe 24 into the downstream-side portion of the same 24.

Then, while the user perceives that a portion of the compressed air in the downstream-side joint 22 of the introduction tube 18 leaks into the atmosphere through the air-leak opening 36, he or she slowly rotates the rotatable member 42 of the pinch-valve device 40 counterclockwise to allow the middle portion of the upstream-side pipe 24 to be elastically restored to its initial shape and thereby slowly increase the cross-sectional area of the middle portion of the pipe 24. More specifically, the user can judge whether the compressed air leaks into the atmosphere via the air-leak opening 36, and whether the amount of leakage of the compressed air is appropriate, by applying his or her fingers over the air-leak opening 36, or sinking the opening 36 in a water to an appropriate depth. That is, those judgments are made based on the sensation of fingers of the user, or whether air bubbles are observed in the water. Thus, the user can slowly increase the amount and pressure of the compressed air that flows in the downstream-side portion of the upstream-side pipe 24 of the tube 18.

At the time when the user perceives that an appropriate amount of compressed air leaks into the atmosphere via the air-leak opening 36, he or she stops rotating the rotatable member 42 of the pinch-valve device 40. In this state, the amount and pressure of the compressed air that flows in the above-indicated downstream-side portion of the upstream-side pipe 24 of the introduction tube 18 are higher as compared with those of the compressed air before the valve device 40 is opened. However, the amount and pressure of the compressed air that flows in the downstream-side portion of the pipe 24 are much lower than those of the compressed air that flows in the upstream-side portion of the pipe 24, and accordingly are very suitable for the air-sucking capability of the air sucker of the particle counter 12.

Then, in the state in which the amount and pressure of the compressed air that flows in the downstream-side portion of the pipe 24 are low enough to be suitable for the air-sucking capability of the air sucker of the particle counter 12, the user operates the number counter of the particle counter 12 to count a number of particles present in the compressed air sucked from the above-indicated downstream-side portion of the introduction tube 18. Then, the user reads the counted particle number displayed on the display 16 of the particle counter 12.

Thus, in the present embodiment, the compressed air introduced from the compressed-air passage 38 into the introduction tube 18 is sucked into the particle counter 12, in the state in which the amount and pressure of the compressed air have been lower to respective appropriate values. Therefore, though the particle counter 12 has no special pressure-resistant structure, the counter 12 is effectively prevented from being damaged or disordered by the pressure of the compressed air sucked. In addition, the counter 12 is advantageously prevented from sucking an excessive amount of air that exceeds a standard amount of air prescribed as being suitable for the counter 12 to count an accurate particle number. Thus, the counter 12 is advantageously prevented from providing an inaccurate counted particle number resulting from the suction of the excessive amount of air. That is, the particle counter 12 can surely provide respective accurate particle numbers.

In addition, in the present embodiment, the user can adjust the degree of flattening of the middle portion of the upstream-side pipe 24 caused by the pinch-valve device 40, while he or she monitors the amount of leakage of the compressed air into the atmosphere through the air-leak opening 36 provided on the downstream side of the middle portion of the pipe 24, i.e., the intermediate portion of the introduction tube 18. Accordingly, the user can easily lower the amount and pressure of the compressed air in the downstream-side portion of the tube 18, located on the downstream side of the middle portion of the pipe 24, to respective appropriate values corresponding to the air-sucking capability of the air sucker of the particle counter 12. Thus, the counter 12 can always provide respective highly reliable counted particle numbers in a stable manner.

Moreover, in the present embodiment, the user can change the amount and pressure of the compressed air in the downstream-side portion of the introduction tube 18, located on the downstream side of the middle portion of the upstream-side pipe 24, by just rotating the rotatable member 42 of the pinch-valve device 40 in the state in which the middle portion of the pipe 24 is positioned between the press plate 74 of the valve member 46, and the lower wall 60 of the support member 44, of the pinch-valve device 40, because the middle portion of the pipe 24 is elastically deformed and the cross-sectional area of the pipe 24 is changed. Thus, the amount and pressure of the compressed air introduced into the introduction tube 18 can be changed with much ease and excellent operability.

Furthermore, in the present embodiment, since the amount and pressure of the compressed air introduced into the introduction tube 18 can be reliably lowered by rotating the rotatable member 42 of the pinch-valve device 40, as described above, the particle-number counting apparatus 10 need not employ a large-capacity and pressure-resistant case for lowering the pressure of the compressed air, in contrast to the previously-described conventional device, and needs only the pinch-valve device 40 that is of much smaller size than the pressure-resistant case. Thus, the present apparatus 10 as a whole enjoys a higher degree of compactness than the conventional device, and accordingly enjoys an improved ease of use or handling.

Thus, in the illustrated embodiment, the amount and pressure of the compressed air introduced into the introduction tube 18 is lowered by just rotating the rotatable member 42 of the pinch-valve device 40, and a number of particles present in the compressed air whose amount and pressure have been lowered is counted by the particle counter 12. Therefore, in contrast to the conventional device in which the large-capacity and pressure-resistant case is used to lower the pressure of the compressed air, the present apparatus 10 need not carry out, before starting counting a number of particles present in the compressed air, a cumbersome and time-consuming preparation operation in which the air remaining in the pressure-resistant case is exchanged with the compressed air. Thus, the present apparatus 10 can more quickly carry out the particle-number counting operation than the conventional device.

In the illustrated embodiment, the introduction tube 18 is provided by just press-fitting the upstream-side and downstream-side pipes 24, 26 in the respective prescribed openings of the upstream-side and downstream-side joints 20, 22. Therefore, when the present particle-number counting apparatus 10 is used to count a number of particles present in a compressed air, the user can exchange the two pipes 24, 26 which had been used in the previous time, with new ones 24, 26, respectively, before he or she connects the tube 18 to the compressed-air passage 38. The exchange of the pipes 24, 26 results in preventing the particles of contaminating matters sticking to the inner surfaces of the pipes 24, 26, from being mixed with the compressed air, and thereby assuring that the particle counter 12 counts an accurate particle number.

Moreover, in the illustrated embodiment, the amount and pressure of the compressed air that flows in the downstream-side portion of the introduction tube 18 are lowered by operating the press plate 74 of the valve member 46, and the lower wall 60 of the support member 44, of the pinch-valve device 40, to externally press, and thereby elastically deform, the upstream-side pipe 24 of the tube 18 so as to decrease the cross-sectional area of the pipe 24. This arrangement effectively prevents the compressed air flowing in the pipe 24, from being contaminated with, e.g., the particles of sticking matter sticking to a device, such as a flow-amount adjusting valve for controlling the amount of flow of the compressed air, which would otherwise be provided inside the pipe 24 to decrease the cross-sectional area of the same 24. Thus, the present apparatus 10 can more accurately count a number of particles present in the compressed air.

The particle-number counting apparatus 10 having the above-described excellent features is advantageously used in a method of constructing a compressed-air cleaning system, by providing one or more particle removing devices at one or more positions, respectively, on a compressed-air supply pipeline which connects between a compressed-air source and one or more compressed-air using devices, so that the particle removing devices remove particles present in a compressed air supplied from the compressed-air source to the compressed-air using devices via the compressed-air supply pipeline, and thereby clean the compressed air.

Figure 4:
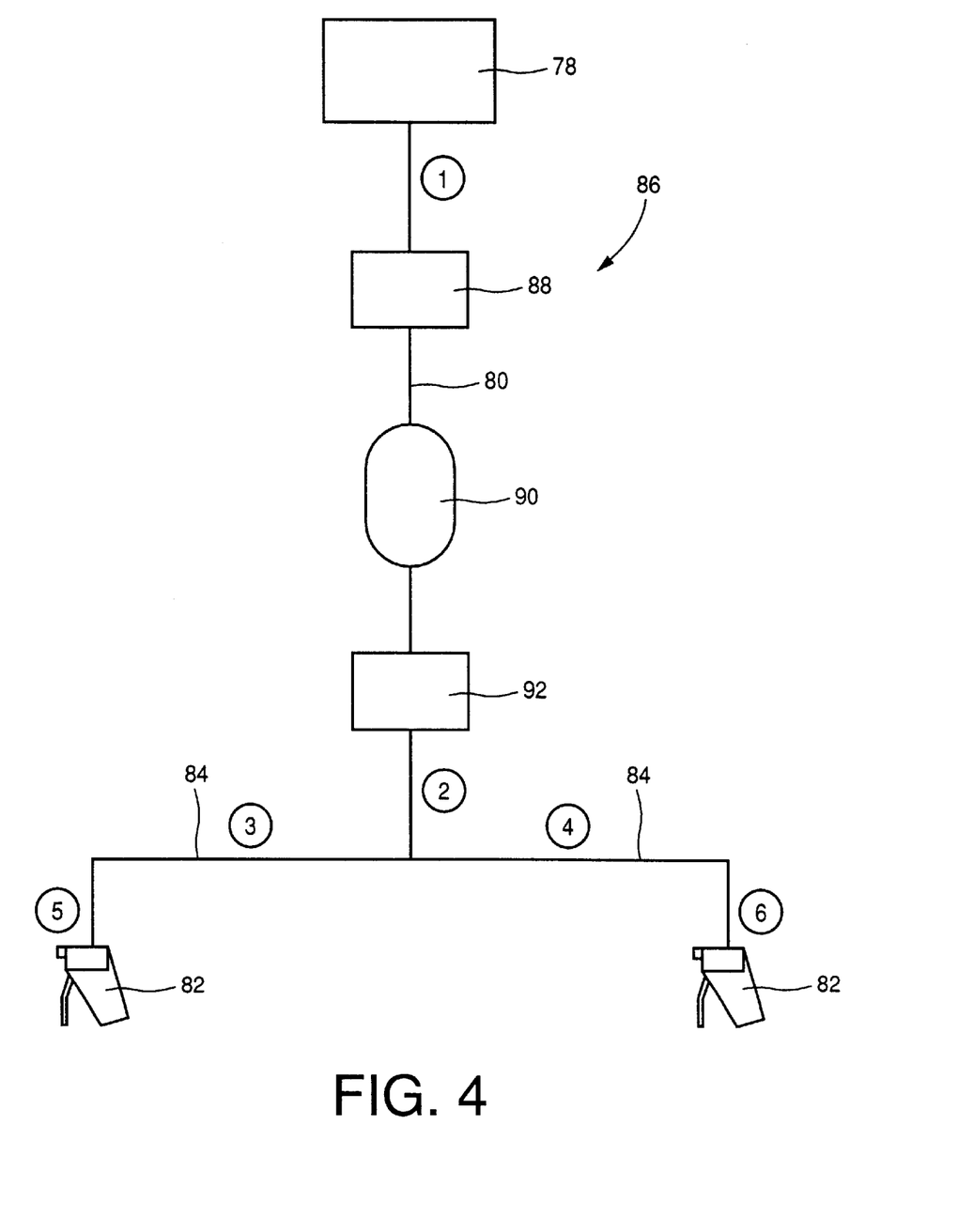
FIG. 4 is a diagrammatic view of a compressed-air supply pipeline which is to be provided with one or more particle removing devices, and thereby constructed into a compressed-air cleaning system, according to a compressed-air-cleaning-system constructing method embodying the present invention.

For example, FIG. 4 shows a compressed-air supply pipeline 86 which includes a main pipe 80 connected to an air compressor 78 as a compressed-air source, and two branch pipes 84, 84 each of which branches from the main pipe 86 and the end of each of which is connected to a so-called air gun 82 as a compressed-air using device. A compressed air produced by the air compressor 78 flows through the main pipe 80 and the two branch pipes 84, 84, and is supplied to each of the two air guns 82, 82. When one or more particle removing devices (not shown) is or are provided on the compressed-air supply pipeline 86, the present method is preferably used for determining an appropriate number of particle removing device or devices to be provided and one or more appropriate positions where the particle removing device or devices are to be provided. In FIG. 4, reference numeral 88 designates an aftercooler which cools the compressed air; numeral 90 designates an air tank which reserves the compressed air; and numeral 92 designates an air drier which removes water vapor from the compressed air.

When one or more particle removing devices is or are provided on the compressed-air supply pipeline 86, the particle-number counting apparatus 10 is used to count a number of particles present in a unit volume of compressed air which flows in the supply pipeline 86. To this end, first, one or more particle-count positions (i.e., measurement positions) is or are determined on the supply pipeline 86. For example, the particle-count position or positions may be determined as a plurality of arbitrary positions which are thought to be effective in measuring the actual condition of contamination of the compressed air that flows in the supply pipeline 86. In the present embodiment, the respective contamination conditions of the compressed air produced by the air compressor 78, the compressed air dried by the air drier 92, the compressed air flowing in the main pipe 80 and/or the branch pipes 84, 84, and the compressed air used by the two air guns 82, 82 at respective ends of the branch pipes 84, 84 (i.e., two ends of the supply pipeline 86), are measured at the following, six particle-count positions: (1) a position on the main pipe 80 on a downstream side of a position where the air compressor 78 is connected to the main pipe 80 (indicated at "1" in FIG. 4), (2) a position on the main pipe 80 on a downstream side of the air drier 92 (indicated at "2"), (3) and (4) respective positions on the two branch pipes 84, 84 between a position where the two branch pipes 84, 84 branch from the main pipe 80 and respective positions where the two branch pipes 84, 84 are connected to the two air guns 82, 82 (indicated at "3" and "4"), and (5) and (6) respective positions on an upstream side of the respective positions where the two branch pipes 84, 84 are connected to the two air guns 82, 82 (indicated at "5" and "6").

Then, the introduction tube 18 of the particle-number counting apparatus 10 is connected to each of the thus selected six particle-count positions on the compressed-air supply pipeline 86, so that the compressed air flowing in each of the main pipe 80 and the branch pipes 84, 84 is introduced into the introduction tube 18 and a number of particles present in the compressed air is counted by operating the counting apparatus 10 in the same manner as described above. Thus, the user obtains six sets of particle-number data each of which is indicative of the counted number of particles present in the compressed air introduced from a corresponding one of the six particle-count positions on the supply pipeline 86, i.e., corresponding six portions of the supply pipeline 86.

Based on the thus obtained six sets of particle-number data, the user determines, on the compressed-air supply pipeline 86, one or more positions where one or more particle removing devices is or are to be provided to be effective in cleaning the compressed air to be supplied to each of the air guns 82, 82. More specifically described, first, the user compares the six counted particle numbers with one another to determine one or more particle-count positions where a significantly great number of particles of the contaminating matter has been counted, and determine one or more particle removing devices which has or have a particle-removing capability corresponding to the counted number of particles. Second, if the user finds one or more particle-count positions where a significantly great number of particles has been counted, he or she can determine at least the one or more particle-count positions as one or more positions where one or more particle removing devices is or are to be provided. If not, the user can determine, to clean effectively the particles present in the compressed air flowing in the supply pipeline 86, the position on the main pipe 80 on the downstream side of the air drier 92 (indicated at "2"), as a representative position on an upstream-side portion of the supply pipeline 86, and the respective positions on the upstream side of the respective positions where the two branch pipes 84, 84 are connected to the two air guns 82, 82 (indicated at "5" and "6"), as representative positions on a downstream-side portion of the supply pipeline 86, as one or more positions where one or more particle removing devices is or are to be provided. However, the manner of determining one or more positions where one or more particle removing devices is or are to be provided, is not limited to that described here, rather the user may arbitrarily determine one or more positions based on the obtained sets of particle-number data. The obtained sets of particle-number data may be processed by a computer to determine automatically one or more positions where one or more particle removing devices is or are to be provided.

Third, the user provides, at the thus determined one or more positions on the compressed-air supply pipeline 86, one or more particle removing devices each of which has a particle-removing capability corresponding to a corresponding one of the counted particle numbers. In the case where two particle removing devices are provided on an upstream-side and a downstream-side portion of the supply pipeline 86, respectively, it is preferred that the particle removing device having the greater particle-removing capability be provided on the upstream-side portion of the supply pipeline 86, because the particles present in the compressed air flowing in the supply pipeline 86 can be more effectively removed. The particle removing device or devices provided on the supply pipeline 86 may be provided by the compressed-air filter device or devices disclosed in U.S. Pat. No. 4,487,618, U.S. Pat. No. 4,897,094, or Registered Japanese Utility Model No. 2,543,671.

Thus, in the present embodiment, the particle-number counting apparatus 10 which can quickly and accurately count a number of particles present in a compressed air is used to count a number of particles present in a compressed air obtained from each of a plurality of positions or portions of the compressed-air supply pipeline 86, and produce sets of particle-number data each of which is indicative of the counted particle number of the compressed air obtained from a corresponding one of the plurality of portions of the supply pipeline 86. Based on the thus obtained sets of particle-number data, the user can determine, on the supply pipeline 86, one or more positions where one or more particle removing devices is or are to be provided and then can actually provide, at the thus determined one or more positions, one or more particle removing devices, respectively. Thus, the user (or the computer) can accurately recognize the actual contamination condition of the compressed air at one or more arbitrary positions on the supply pipeline 86 and can provide, according to the thus recognized contamination condition of the compressed air, an appropriate number of particle removing device or devices at one or more appropriate positions on the supply pipeline 86. Accordingly, the compressed air flowing in the supply pipeline 86 can be more effectively and more reliably cleaned.

While the present invention has been described in its preferred embodiments, those emodiments are just examples, and the present invention is by no means limited to the details of those embodiments but may be otherwise embodied.

For example, although in the embodiment shown in FIG. 1 the particle counter 12 which counts a number of particles present in a compressed air is provided by a laser particle counter for use in counting a number of particles present in an air under normal pressure, the particle counter 12 may be provided by any selected one of various known devices each of which has both the mechanism or fuction of sucking air from outside and the mechanism or function of counting a number of particles present in air.

In the embodiment shown in FIG. 1, the introduction tube 18 is provided by the upstream-side joint 20 to be connected to the compressed-air passage 38; the upstream-side pipe 24 connected to the joint 20; the downstream-side pipe 26 connected to the suction inlet 15 of the particle counter 12; and the downstream-side joint 22 which connects the two pipes 24, 26 to each other to communicate the two pipes 24, 26 with each other and which has the air-leak opening 36 opening in the atmosphere. However, the structure of the introduction tube 18 is not limited to that, but rather the tube 18 may be provided by any one having a structure which assures that the compressed air in the compressed-air passage 38 is introduced to the suction inlet 15 of the particle counter 12 and a portion of the compressed air is allowed to leak into the atmosphere. The introduction tube 18 may have a structure which is provided by a plurality of members, or a structure which is provided by a single member.

The above-indicated respective constituent members 20, 22, 24, 26 of the introduction tube 18 may be formed of respective materials other than those described in connection with the illustrated embodiments. The introduction tube 18 may be formed of any material which assures that the tube 18 allows the pinch-valve device 40 as the pressure lowering device to sandwich a portion thereof, that portion is elastically deformed when being externally pressed by the pinch-valve device 40, and the tube 18 can stand the pressure of the compressed air flowing therein.

Moreover, in the embodiment shown in FIGS. 2 and 3, the pressure lowering device is provided by the pinch-valve device 40 including the rotatable member 42; the support member 44 by which the rotatable member 42 is rotatably supported; and the valve member 46 which is opposed to a portion of the support member 44 and which is screwed in the rotatable member 42. When the rotatable member 42 is rotated by the user, the valve member 46 is moved downward, so that the intermediate portion of the introduction tube 18 is vertically pressed by, and between, respective opposed portions of the valve member 46 and the support member 44 that are vertically opposed to each other. Thus, the intermediate portion of the tube 18 is elastically deformed to decrease the cross-sectional area of the tube 18. However, the structure of the pressure lowering device is not limited to that described above. Rather, the pressure lowering device may be provided by any device having such a structure which assures that the device externally presses, and elastically deforms, the intermediate portion of the introduction tube 18 to decrease the cross-sectional area of the intermediate portion, and thereby decrease the amount of the compressed air that flows in a downstream-side portion of the tube 18 on a downstream side of the intermediate portion, so that a pressure of the compressed air flowing in the downstream-side portion of the tube 18 is lower than a pressure of the compressed air flowing in an upstream-side portion of the tube 18 on an upstream side of the intermediate portion in a flow direction in which the compressed air flows in the tube 18. Accordingly, the pressure lowering device may be provided by, in place of the pinch-valve device 40 employed in the illustrated embodiments, a spring member, such as a pinchcock, which externally presses, and elastically deforms, the intermediate portion of the introduction tube 18, owing to its elastic restoring force; or one of various elastic band members each of which externally tightens or binds, and elastically deforms, the intermediate portion of the introduction tube 18.

It is to be understood that the present invention may be embodied with other changes, improvements, and modifications that may occur to a person skilled in the art without departing from the scope and spirit of the invention defined in the appended claims.

What is claimed is:

1. An apparatus for counting a number of particles present in a compressed air introduced from a compressed-air passage, the apparatus comprising:

an introduction tube which is elastically deformable and which is connected to the compressed-air passage to introduce the compressed air therefrom;

a pressure lowering device which is provided at a position corresponding to an intermediate portion of the introduction tube, and which externally presses, and thereby elastically deforms, the intermediate portion of the tube to decrease a cross-sectional area of said intermediate portion, and thereby decrease an amount of the compressed air that flows through a downstream-side portion of the tube that is located on a downstream side of said intermediate portion in a flow direction in which the compressed air flows in the tube, so that a pressure of the compressed air in the downstream-side portion of the tube is lower than a pressure of the compressed air in an upstream-side portion of the tube that is located on an upstream side of said intermediate portion in the flow direction;

the introduction tube having an air-leak opening which is provided in the downstream-side portion thereof and which allows a portion of the compressed air in said downstream-side portion to leak into an atmosphere; and a particle-number counter which sucks, in a state in which said portion of the compressed air in the downstream-side portion of the introduction tube is allowed to leak into the atmosphere via the air-leak opening, the compressed air in said downstream-side portion and counts a number of particles present in the sucked compressed air.

2. An apparatus according to claim 1, wherein the pressure lowering device comprises:

two members which are provided on both sides of the intermediate portion of the introduction tube such that the two members are opposed to each other via said intermediate portion and are movable toward, and away from, each other; and an operable member which is operable to move the two members toward, and away from, each other, wherein when the operable member is operated to move the two members toward each other, the two members sandwich, and thereby elastically deform, the intermediate portion of the introduction tube to decrease the cross-sectional area of said intermediate portion.

3. A method of counting a number of particles present in a compressed air, by using a particle-number counter which sucks the compressed air introduced from a compressed-air passage and counts the number of particles present in the sucked compressed air, the method comprising the steps of:

connecting an elastically deformable, introduction tube to the compressed-air passage, to introduce the compressed air from the passage into the tube, externally pressing, and thereby elastically deforming, an intermediate portion of the introduction tube to decrease a cross-sectional area of said intermediate portion, and thereby decrease an amount of the compressed air that flows through a downstream-side portion of the tube that is located on a downstream side of said intermediate portion in a flow direction in which the compressed air flows in the tube, so that a pressure of the compressed air in the downstream-side portion of the tube is lower than a pressure of the compressed air in an upstream-side portion of the tube that is located on an upstream side of said intermediate portion in the flow direction, and operating, in a state in which a portion of the compressed air in the downstream-side portion of the introduction tube is allowed to leak into an atmosphere via an air-leak opening provided in said downstream-side portion, the particle-number counter to suck the compressed air in said downstream-side portion and count a number of particles present in the sucked compressed air.

4. A method of constructing a compressed-air cleaning system, by providing at least one removing device at at least one position on a compressed-air supply pipeline which connects between a compressed-air source and at least one compressed-air using device, so that the removing device removes particles present in a compressed air supplied from the compressed-air source to the compressed-air using device via the compressed-air supply pipeline, and thereby cleans the compressed air, connecting an elastically deformable, introduction tube to each of a plurality of arbitrarily selected portions of the compressed-air supply pipeline, to introduce the compressed air from the pipeline into the tube, externally pressing, and thereby elastically deforming, an intermediate portion of the introduction tube to decrease a cross-sectional area of said intermediate portion, and thereby decrease an amount of the compressed air that flows through a downstream-side portion of the tube that is located on a downstream side of said intermediate portion in a flow direction in which the compressed air flows in the tube, so that a pressure of the compressed air in the downstream-side portion of the tube is lower than a pressure of the compressed air in an upstream-side portion of the tube that is located on an upstream side of said intermediate portion in the flow direction, operating, in a state in which a portion of the compressed air in the downstream-side portion of the introduction tube is allowed to leak into an atmosphere via an air-leak opening provided in said downstream-side portion, a particle-number counter to suck the compressed air in said downstream-side portion and count a number of particles present in the sucked compressed air, so as to obtain a plurality of sets of particle-number data each of which is indicative of the counted number of particles present in the compressed air introduced from a corresponding one of said plurality of portions of the compressed-air supply pipeline, determining, based on the obtained sets of particle-number data, said at least one position on the compressed-air supply pipeline where said at least one removing device is to be provided to effectively clean the compressed air to be supplied to the compressed-air using device, and providing said at least one removing device at the at least one determined position on the compressed-air supply pipeline.

5. A method according to claim 4, wherein the compressed-air supply pipeline comprises a main pipe which is connected to the compressed-air source, and a plurality of branch pipes each of which is connected to the main pipe and which are connected to a plurality of compressed-air using devices, respectively.

* * * * *